United States Patent [19]

Gendler

[11] Patent Number: 4,932,973

[45] Date of Patent: Jun. 12, 1990

[54] CARTILAGE AND BONE INDUCTION BY ARTIFICIALLY PERFORATED ORGANIC BONE MATRIX

[76] Inventor: El Gendler, 2519 S. Flower, Los Angeles, Calif. 90007

[21] Appl. No.: 186,696

[22] Filed: Apr. 21, 1988

Related U.S. Application Data

[63] Continuation of Ser. No. 905,572, Sep. 9, 1986, abandoned, which is a continuation-in-part of Ser. No. 537,687, Sep. 30, 1983, abandoned.

[51] Int. Cl.$^5$ .............................................. A61F 2/38
[52] U.S. Cl. ........................................ 623/16; 623/66
[58] Field of Search ....................... 623/10, 11, 16, 18, 623/22, 23, 66; 128/1 R

[56] References Cited

U.S. PATENT DOCUMENTS

| | | | |
|---|---|---|---|
| 3,852,045 | 12/1974 | Wheeler et al. | 623/16 |
| 4,330,891 | 5/1982 | Branemark et al. | 128/92 W |
| 4,553,272 | 11/1985 | Mears | 623/1 |

FOREIGN PATENT DOCUMENTS 2821354  11/1978  Fed. Rep. of Germany ........ 623/16

OTHER PUBLICATIONS

Holmes; "Bone Regeneration within a Cotallene Hydroxapatite Implant" Plastic & Reconstructure Surgery, vol. 63, No. 5, May 1979.
"Application of the Biological Principal of Induced Osteogenesis for Craniofacial Defects", by Julie Glowacki et al., The Lancet, May 2, 1981.
"Demineralized Bone Implants", by Julie Glowacki et al., Clinics in Plastic Surgery, vol. 12, No. 2, Apr. 1985.
"Use of Demineralized Allogenic Bone Implants for the Correction of Maxillocraniofacial Deformities", by John B. Mulliken, M. D.
"Chemosterilized Antigen-Extracted Surface-Demineralized Autolysed Allogenic (AAA) Bone for Arthrodesis", by Marshall R. Urist.

*Primary Examiner*—David J. Isabella
*Attorney, Agent, or Firm*—Leydig, Voit & Mayer

[57] ABSTRACT

A process of encouraging induction of cartilage and bone formation by organic bone matrix. The process involves forming a plurality of continous channel perforations in organic bone matrix prior to the implantation of same. These perforations become centers of cartilage and bone induction after the implantation of bone matrix and produce a significant increase in the ability of bone matrix to induce cartilage and bone formation.

2 Claims, 1 Drawing Sheet

CARTILAGE AND BONE INDUCTION BY ARTIFICIALLY PERFORATED ORGANIC BONE MATRIX

This application is a continuation of application Ser. No. 905,572, filed Sept. 9, 1986, now abandoned which is a continuation-in-part of application Ser. No. 537,687, filed Sept. 30, 1983, now abandoned.

BACKGROUND OF THE INVENTION

1. Field of the Invention

The present invention relates to a process of formation of multiple centers of cartilage and bone induction and more particularly to a process of preparing organic bone matrix by forming artificial perforations, in the form of continuous channels, therein which perforations become centers of cartilage and bone induction after the implantation of said organic bone matrix, and to product, such as the artificially perforated organic bone matrix, obtained by the process taught herein. The invention involves forming multiple artificial perforations having the form of continuous channels in organic bone matrix prior to said organic bone matrix surgical implantation in order to produce formation of multiple centers of cartilage and bone induction after the implantation of same and to produce a significant increase in the ability of the implanted material to induce cartilage and bone formation.

2. Description of the Prior Art

As is known, bones and teeth are composed of a matrix of organic material consisting of collagenous fibrils and a binding substance of mucopolysaccharides as well as of the inorganic component, namely calcium phosphate in the form of hydroxyapatite. The organic matrix is formed by filiform molecules arranged parallel to each other. Furthermore, the tissue is transversed by numerous microscopic capillaries which are oriented in various directions to said filiform molecules.

It is known that if the inorganic component is partially or completely removed from the bone or tooth, the remaining organic bone material, called organic bone matrix, can be transplanted to other living animal or human bodies without substantial deleterious effects. Consequently, bone matrix is used in modern medical procedures for its ability to induce formation of cartilage and bone after its implantation into a body site (this phenomena is known as "osteoinduction").

While the prior art has recognized the need for methods to stimulate osteoinduction and for material with augmented ability to induce cartilage and bone formation, none have disclosed the unique process of the herein disclosed invention.

Myers, et al. Pat. No. 3,458,397 is directed to a process for producing osteogenic material from animal bone tissue. The osteogenic material is injected into an animal for the purpose of inducing bone formation. In this process, the bone is comminuted with pepsin in an acid solution and then digested, extracted and precipitated. There is no suggestion in this reference, however, of artificially perforating the bone matrix as is taught herein.

Urist Pat. No. 4,294,753 is directed to a bone morphogenetic protein process for separating proteins from bone tissue. As in the previous reference, this reference calls for a comminution of the bone and the demineralization of the bone tissue The demineralized bone tissue is then treated in an aqueous solution with a water soluble, neutral salt and a solubilizing agent. The neutral salt and the solubilizing agent are then separated, and the bone morphogenetic protein is precipitated. Once again, no mention of any type of perforation in the produced substance is shown.

Sano Pat. No. 2,621,145 is directed to bone mat compositions and includes particulates of bone which are then enmeshed in a fibrin network. This produces a bone mat which is supported on a carrier strip stated to be of a flexible, plastic material. The process taught in this reference produces a flexible strip for use in bone surgery and promoting the regrowth of bone and includes what is termed a plurality of unboiled particles of ground, whole bone enmeshed in a fibrin network. This reference does not provide for perforating the bone mat composition or fibrin network as is taught herein.

Rapkin Pat. No. 2,968,593 describes a method of preparing inorganic bone material by heating animal bone material in a liquid to a temperature from about 80° C. to about 100° C., drying the heated bone material, substantially defattening it wih a fat-extracting solvent, and removing the organic matrix from the defattened bone material, for instance, by extraction with ethylene diamine to obtain the inorganic matrix. Such an inorganic bone material which is free of organic matter is used for transplantation from an animal of one species to another species without any adverse effect. However, there is no provision taught in the reference for perforating the inorganic bone material so produced.

Thiele, et al. Pat. No. 4,172,128 is directed to a process of degrading/regenerating bone and tooth material. This reference provides a method of making a bone material which is implanted into an area to stimulate bone growth. In this reference the bone material is first ground and then the organic matrix of the bone is demineralized. A colloidal solution of the organic matrix is formed and ions are caused to diffuse into the colloidal solution in order to form a gel. Although the substance created through this process appears to be used for osteogenesis, this reference does not provide for perforating said substance as is taught herein.

Koster et al Publication *Langenbecks Archiv fur Chirurgie* v. 341, p. 77–86, 1976 described ceramic bone implants with various Ca/P ratio and pores that do not extend through the implant. After this ceramic is implanted into bone defects it demonstrates bone ingrowth (the bone sprouting from the fracture ends grows inside the ceramic channels) and the ceramic becomes gradually resorbed. This reference does not teach about the process for the formation of multiple centers of cartilage and bone induction, neither does it teach about organic bone matrix with multiple perforations in the form of continuous channels which perforations become individual centers of cartilage and bone induction (cartilage and bone are formed de novo without any connection to previously existing sources of cartilage or bone).

SUMMARY AND OBJECTS OF THE INVENTION

It is one object of the invention to provide a novel process of producing multiple centers of cartilage and bone induction through the implantation of artificially perforated organic bone matrix by forming a plurality of artificial perforations in the organic bone matrix, implanting the said perforated organic bone matrix, the artificially perforated organic bone matrix being readily accepted by the body and said perforations becoming centers of cartilage and bone induction.

Another object of the present invention is to provide such novel and valuable artificially perforated organic bone matrix useful as the material with the increased ability to induce cartilage and bone after implantation inside the body, and as a material able to produce multiple centers of cartilage and bone induction after implantation.

Other objects of the present invention and advantageous features thereof will become apparent as the description proceeds.

In principle, in a process of cartilage and bone induction by implantation of organic bone matrix, the improvement of the present invention comprises adding a step of forming a plurality of artificial perforations having the form of continuous channels in the organic bone matrix prior to implantation of same inside the body which perforations become multiple centers of cartilage and bone induction.

Another embodiment of the invention is the artificially perforated organic bone matrix produced in accordance with the process of the invention taught herein.

DESCRIPTION OF THE BEST EMBODIMENTS CONTEMPLATED

Referring to the figures of drawings wherein like numbers of reference designate like elements throughout, the present invention is directed to an improvement in the process for the production of cartilage and bone induction by the implantation of organic bone matrix which comprises adding a step of forming a plurality of artificial perforations having the form of continuous channels in said organic bone matrix prior to the implantation of same, said perforations becoming the multiple centers of cartilage and bone induction after the implantation inside the body.

Organic bone matrix may be produced using any one of the known prior art methods which may include any combination of the following steps.

Figure 1:
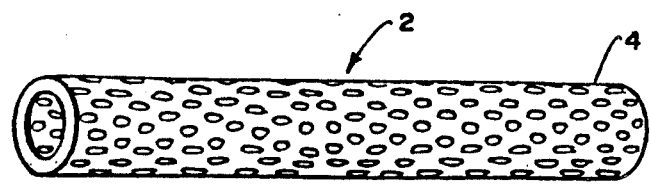
FIG. 1 is a side elevational view of a organic bone matrix having a plurality of artificial perforations therein.
Figure 1A:
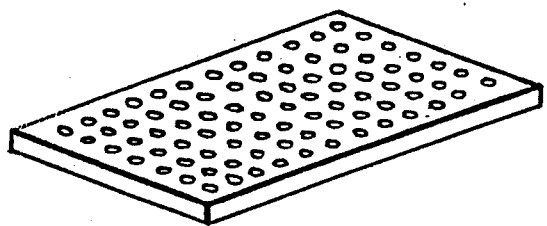
FIG. 1a is a side elevational view of an alternately formed organic bone matrix having a plurality of artificial perforations therein.

A whole bone or a part of the bone is harvested from any of the vertebrates. It can be then be conserved by any of the known conservation methods. Partial or complete demineralization of the bone is carried out to cause decalcification by subjecting the bone to treatment with different acids, chelating agents, electrolysis or any combination of the foregoing. Finally, either prior to or after the demineralization of the bone, fixation and different physical and chemical processing is done. The prepared bone or organic bone matrix 2, shown in FIG. 1, is then processed to form a plurality of artificial perforations in the form of continuous channels 4 therein.

The plurality of perforations 4 may be formed in organic bone matrix 2 by drilling, laser, puncture or the like process. Perforations 4 may be of various shapes, such as, but not limited to, circular, triangular, multi-angled, irregular, slit-like or any combination of the foregoing. Preferably the perforations, in the form of continuous channels, extend from one surface of the matrix 2 to the opposite surface.

The number of perforations 4 in organic bone matrix 2 may vary. Multiple perforations, however, produce a substantial increase in the ability of the perforated organic bone matrix to induce cartilage and bone formation after the implantation because each perforation becomes an individual center of cartilage and bone induction.

Figure 1B:
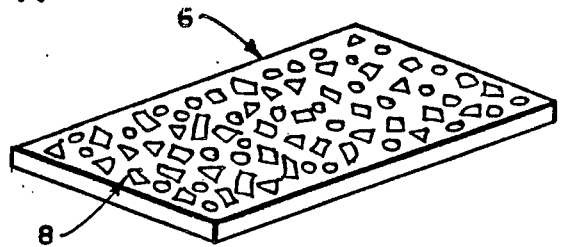
FIG. 1b is a side elevational view of an alternately formed organic bone matrix having a plurality of artificial perforations therein of varying sizes and shapes.

Neither must the perforations be of a uniform size or shape in the organic bone matrix. FIG. 1b shows an alternately shaped organic bone matrix 6 having a plurality of varying shaped and sized perforations 8 therein It has been noted, however, that perforations having a maximum cross sectional area of 0.25 mm. to 1.0 mm. are optimally sized perforations to become a center of cartilage and bone induction after the implantation and thus substantially increase the ability of the artificially perforated organic bone matrix to induce cartilage and bone formation.

Similarly, the perforations need not be uniformly concentrated over the surface area of the bone matrix. In fact, a higher concentration of perforations in a given area of the bone matrix will cause greater induction of cartilage and bone in that particular area comparing to other areas having a lower concentration of perforations.

The perforated organic bone matrix as taught herein can be used in medicine to produce multiple centers of cartilage and bone induction after the implantation inside the body. The following specific examples serve to illustrate the present invention without, however, limiting the same thereto.

EXAMPLE ONE

A laboratory-controlled test was performed to examine the induction of cartilage and bone formation by implantation of perforated organic bone matrix in laboratory test animals. A perforated organic bone matrix was prepared in accordance with the invention taught herein and was implanted subcutaneously lateral to the sternal edge of each laboratory test rat chosen to form a test group.

Four days after the implantation procedures were accomplished, a sample of laboratory rats from the test group was prepared and samples taken of the implantation site. Under microscopic examination, it was found that inside the perforations of the implanted organic bone matrix, there was an accumulation of newly formed undifferentiated cells with a high activity of alkaline phosphatase in their cytoplasm.

Seven days after the implantation was accomplished, a further sample of laboratory rats from the test group was prepared and samples taken of the implantation site. Under microscopic examination, it was found that there was a small number of differentiated cartilage cells inside the perforations Cartilage cells had high alkaline phosphatose activity in their cytoplasma.

Ten days after the implantation was accomplished another sample of laboratory rats from the test group was prepared and samples taken of the implantation site. Under miscroscopic examination it was found that the majority of perforations were filled with cartilage. In some perforations the ingrowth of newly formed capillaries produced partial cartilage resorption and new bone formation was taking place.

Two weeks after the implantation was accomplished, another sample of laboratory rats from the test group was prepared and samples taken of the implantation site. Under microscopic examination, it was found that some bone matrix resorption around the edges of the perforations had occurred. The perforations were filled with newly formed bone trabeculae covered with osteoblasts. The trabecular bone was interspaced with islands of cartilage tissue and newly formed blood vessels. Also, the alkaline phosphatase activity in the cells filling the perforations was very high.

One month after the implantation was accomplished, a sample of laboratory rats from the test group was prepared and samples taken of the implantation site. Under microscopic examination it was found that the main part of the implanted perforated bone matrix had undergone resorption and had been replaced by newly formed trabecular bone interspaced with occasional islands of cartilage tissue. Newly formed trabecular bone was not restricted to previously implanted perforated bone matrix, but was seen beyond this area and surrounded with a capsule resembling the periosteum.

EXAMPLE TWO

This test examined the stimulation of bone regeneration by the implantation of perforated organic bone matrix. Several laboratory rabbits were chosen to form a test group. The rabbits each had a piece of ulnar bone approximately 1.5 to 2 cm. removed from the mid-shaft of the ulnar bone and a fragment of perforated organic bone matrix prepared in accordance with the procedure taught herein inserted into the defect. Control x-rays taken immediately following the implantation procedure clearly showed the bone defect.

One week after the implantation, x-ray examination of the implantation site still showed the defect in the ulnar bone clearly. A sample of rabbits from the test group was prepared and samples taken of the implantation site. Under microscopic examination it was found that all the perforations of the implanted perforated organic bone matrix were filled with young undifferentiated cells with high activity of alkaline phosphatase.

Two weeks after the implantation, x-ray examination showed a small amount of mineralization in the area of implanted perforated organic bone matrix. A sample of rabbits taken from the test group was prepared and samples taken of the implantation site. Under microscopic analysis it was found that all perforation were filled with cartilage interspaced with newly formed bone trabeculae.

One month after the implantation, x-ray examination showed that the implanted perforated organic bone matrix had undergone mineralization. A sample of rabbits from the test group was prepared and samples taken of the implantation site. Under miscroscopic analysis it was found that the implanted perforated organic bone matrix had undergone resorption which had been spreading from centers established inside the perforations. It was also found that the implanted organic bone matrix was being replaced by newly formed trabecular bone which was connected with the trabecular bone growing from the ends of the bone fragments.

Two months after the implantation, x-ray examination showed that the defect in the ulnar bone of the test rabbits had been replaced by highly mineralized bone tissue. A final sampling of rabbits from the test group was prepared and samples taken of the implantation site. Under microscopic analysis it was found that the ulnar bone defect had now been filled with bone undergoing remodeling.

EXAMPLE THREE

This test examined the formation of cartilage and bone induction centers by perforated organic bone matrix having different sized perforations. A bone matrix was prepared as in Example One, in accordance with the procedure taught herein, with perforations of different diameter: 0.25 mm.; 0.35 mm; 0.5 mm.; 0.75 mm.; 1.0 mm.; 1.25 mm.;1.5 mm. and 2.0 mm. The perforated organic bone matrix was implanted subcutaneously in laboratory rats as outlined in Example One. At different times following the implantation, a sample of laboratory rats from the test group was prepared and samples taken of the implantation site. Microscopic analysis of the implanted organic bone matrix showed that the most active process of formation of cartilage and bone induction centers was seen in specimens having a perforation diameter of 0.25 to 0.5 mm. In specimens with perforation diameter of 0.75 to 1.0 mm, cartilage and bone induction was somewhat less active and in specimens with perforation diameter of 1.25 to 2.0 mm., it was even less active.

The invention described above is, of course, susceptible of many variations and modifications, all of which are within the skill of the art. It should be understood that all of such variations and modifications are within the spirit and scope of the invention and of the appended Claims. Similarly, it will be understood that it is intended to cover all changes and modifications of the examples of the invention herein disclosed for the purpose of illustration which do not constitute departures from the spirit and scope of the invention.

I claim:

1. A method for inducing the formation of bone and cartilage within a body comprising implanting within said body a matrix material which consists essentially of organic bone matrix having discrete predetermined perforations, said matrix, after implantation within said body, being capable of initially accumulating undifferentiated cells within said perforations and subsequently stimulating the transformation of said cells into differentiated cartilage and bone cells, independent of any bone or cartilage ingrowth from preexisting sources of cartilage or bone tissue.

2. An implant for inducing the formation of bone and cartilage within a body, said implant consisting essentially of organic bone matrix having discrete predetermined perforations; the perforations of the matrix, after implantation within said body, being capable of initially accumulating differentiated cells within said perforations and subsequently stimulating the transformation of said cells into differentiated cartilage and bone cells, independent of any bone or cartilage ingrowth from preexisting sources of cartilage or bone tissue.

* * * * *